United States Patent [19]

Latham et al.

[11] Patent Number: 5,599,938
[45] Date of Patent: Feb. 4, 1997

[54] PROCESS FOR PREPARING A PIPERIDINE DERIVATIVE

[75] Inventors: David W. S. Latham; Michael D. Goodyear; Andrew J. Whitehead, all of Ware, Great Britain

[73] Assignee: Glaxo Group Limited, London, England

[21] Appl. No.: 287,910

[22] Filed: Aug. 9, 1994

[30] Foreign Application Priority Data

Aug. 13, 1993 [GB] Great Britain .......................... 9316863

[51] Int. Cl.$^6$ ................................................. C07D 211/56
[52] U.S. Cl. ............................................. 546/224; 546/223
[58] Field of Search ...................................... 546/224, 223

[56] References Cited

U.S. PATENT DOCUMENTS

| | | | |
|---|---|---|---|
| 3,998,834 | 12/1976 | Janssen et al. | 260/293.68 |
| 4,179,569 | 12/1979 | Janssen | 546/223 |
| 5,019,583 | 5/1991 | Feldman et al. | 514/327 |

FOREIGN PATENT DOCUMENTS 0160422  11/1985  European Pat. Off. .

OTHER PUBLICATIONS

Feldman et al., *J. Org. Chem.*, 1990, 55, 4207–4209.
Taber et al., *J. Org. Chem.*, 1992, 57, 4037–4038.
Van Daele et al., *Arzneim.–Forsch.*, 1976, 26(8), 1521–1531.

Primary Examiner—C. Warren Ivy
Assistant Examiner—Raymond Covington
Attorney, Agent, or Firm—Bacon & Thomas

[57] ABSTRACT

A process for the preparation of the compound of formula (I), a useful intermediate for the preparation of analgesic agents.

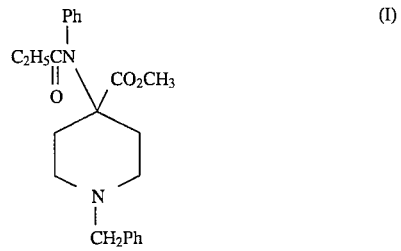

which comprises reading a compound of formula (II) or an acid addition salt thereof

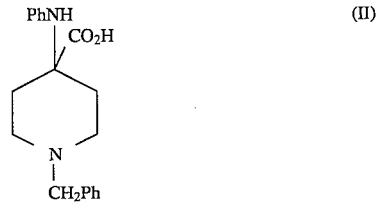

with propionic anhydride and then treating the resultant product with methanol.

10 Claims, No Drawings

PROCESS FOR PREPARING A PIPERIDINE DERIVATIVE

This invention relates to a process for preparing a piperidine derivative which is useful in the preparation of compounds having analgesic activity.

A number of N-phenyl-N-(4-piperidinyl)amide derivatives have been described as analgesics and examples of such compounds are described in U.S. Pat. Nos. 3,998,834 and 5,019,583. A subclass of these N-phenyl-N-(4-piperidinyl)amide derivatives having analgesic activity are those containing the grouping

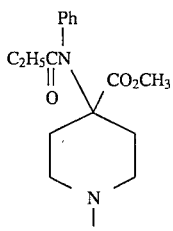

and such compounds are conveniently prepared from the N-benzyl compound (I)

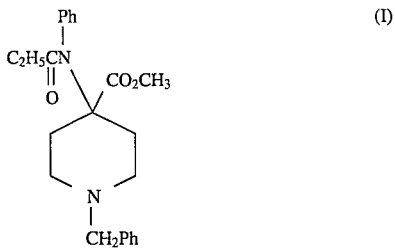

U.S. Pat. No. 3,998,834 specifically teaches that the N-benzyl compound (I) may be prepared from the carboxylic acid (II) by the route outlined below.

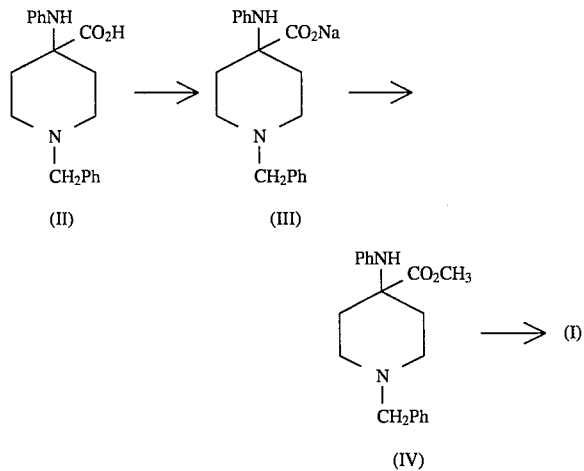

The carboxylic acid (II) is converted into the corresponding sodium salt (III) which is then reacted with methyl iodide to give the ester (IV). Reaction of the ester (IV) with propionic anhydride then yields the required N-benzyl compound (I) which is purified by column chromatography.

The present invention relates to an improved process for preparing the N-benzyl compound (I) from the carboxylic acid (II) in a high yield. Furthermore the process has the advantage that relatively low reaction temperatures may be used, short reaction times, a simple isolation procedure and avoids the use of toxic reagents (methyl iodide or dimethyl sulphate) and thus is particularly convenient for the large scale manufacture of (I).

Accordingly the present invention provides a process for the preparation of the N-benzyl compound of formula (I) which comprises reacting the carboxylic acid (II) or an acid addition salt thereof with propionic anhydride and the reaction of the resultant product with methanol.

The reaction of the compound of formula (II) with propionic anhydride is conveniently carried out in an aprotic solvent such as a hydrocarbon e.g. toluene or an ester e.g. ethyl acetate or isopropyl acetate and preferably in the presence of a base. Examples of suitable bases include tertiary amines such as trialkylamines e.g. triethylamine or heteroaryl amines e.g. pyridine. This reaction is also conveniently carried out at a temperature within the range 15°–120° e.g. 15°–80° and more particularly at ambient temperature or with heating e.g. 50°–80°.

The subsequent reaction with methanol is conveniently carried out without prior isolation of the product of the reaction of the compound of formula (II) with propionic anhydride, and this reaction is preferably carried out with heating e.g. 50°–80°.

In a preferred aspect of the invention, the compound of formula (II) or an acid addition salt thereof is reacted with an excess of propionic anhydride in an aprotic solvent such as ethyl acetate and in the presence of an excess of the tertiary base e.g. triethylamine and at a reaction temperature between 15°–80° e.g. ambient temperature or with heating e.g. 50°–80°. The product of this reaction without prior isolation is then reacted with methanol and conveniently. this reaction is carried out with heating e.g. 50°–80° C.

The compound of formula (I) is conveniently isolated in the form of an acid addition salt thereof and in particular an oxalate salt thereof.

The compound of formula (I) and acid addition salts thereof is a particularly useful intermediate for preparing compounds described in U.S. Pat. No. 5,019,583 and in particular 3-[4-methoxycarbonyl-4-[(1-oxopropyl)phenylamino]-1-piperidine]propanoic acid, methyl ester and acid addition salts thereof e.g. the hydrochloride. A particularly convenient method for preparing 3-[4-methoxycarbonyl-4-[(1-oxopropyl)phenylamino]-1-piperidine]propanoic acid methyl ester from the compound of formula (I) is described in U.S. Pat. No. 5,019,583.

Thus the present invention also provides 3-[4-methoxycarbonyl-4-[(1-oxopropyl)phenylamino]-1-piperidine]propanoic acid methyl ester and acid addition salts thereof whenever prepared from a compound of formula (I) or a salt thereof wherein the compound of formula (I) has been prepared from a compound of formula (II) by reaction with propionic anhydride and then methanol as described above.

In order that the invention may be more fully understood the following examples are given by way of illustration only.

EXAMPLE 1

Methyl 4-[N-(1-oxopropyl)-N-phenylamino]-1-(phenylmethyl)-4-piperidinecarboxylate oxalate A suspension of (4-phenylamino)-1-(phenylmethyl)-4-piperidine carboxylate hydrochloride (3.93 kg) in ethyl acetate (25.5 l) was treated with propionic anhydride (8.7 l) washed in with ethyl acetate (2 l) and the suspension heated to reflux. Triethylamine (4.7 l) was added, washed in with ethyl acetate (2 l) and the mixture held at reflux for 1 h. Methanol (7.9 l) was added to give a clear solution, which was heated at reflux for a further 2 h and cooled to room temperature. 5M sodium hydroxide solution (22 l) was added and the phases were separated. The aqueous phase was extracted with ethyl acetate (20 l). The combined organic phase extracts were washed with 2M sodium hydroxide solution (20 l) and water (2×20 l). The organic phase was treated with water (20 l) and phosphoric acid solution (2.5M, 10.5 l) was added until the pH of the aqueous phase was 6.1. The phases were separated and the aqueous phase discarded. A solution of oxalic acid (1.14 kg) in methanol (4 l) was added to the organic phase to give a white suspension which was stirred for 1 h, filtered and the product washed with ethyl acetate (2×4 l) and dried to give the title compound (4.543 kg).

EXAMPLE 2

Methyl 4-[N-(1-oxopropyl)-N-phenylamino]-1-(phenylmethyl)-4-piperidinecarboxylate oxalate A suspension of (4-phenylamino)-1-(phenylmethyl)-4-piperidine carboxylate hydrochloride (20 g), and propionic anhydride (52 ml) in ethyl acetate (150 ml) was treated with triethylamine (24 ml) and the mixture was stirred at ambient temperature for 16 h. The suspension was heated to about 60°, and methanol (40 ml) was added to give a clear solution, which was heated at reflux for a further 3 h. The solution was cooled to room temperature, sodium hydroxide solution (5M, 112 ml), was added, and the phases were separated. The aqueous phase was extracted with ethyl acetate (100 ml). The combined organic extracts were washed with sodium hydroxide solution (2M, 100 ml) and water (2×100 ml). The organic phase was treated with water (100 ml) and then phosphoric acid solution (25% w/v, ca 35 ml) was added until the pH of the aqueous phase was 6.0–6.2. The phases were separated and the aqueous phase was discarded. A solution of oxalic acid dihydrate (7.26 g) in methanol (20 ml) was added to give a white suspension. The suspension was stirred for 40 min and filtered. The product was washed with ethyl acetate (2×20 ml) and dried in vacuo at 45° overnight to give the title compound (24 g).

We claim:

1. A process for the preparation of the compound of formula (I)

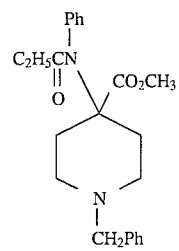

which comprises reading a compound of formula (II) or an acid addition salt thereof

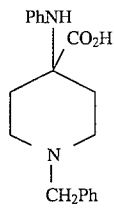

with propionic anhydride and then treating the resultant product with methanol.

2. A process as claimed in claim 1 wherein the reaction is carried out in the presence of a base.

3. A process as claimed in claim 2 wherein the base is a tertiary amine.

4. A process as claimed in any of claim 1 wherein the reaction of the compound of formula (II) with propionic anhydride is carried out in an aprotic solvent.

5. A process as claimed in any of claim 1 wherein the reaction is carried out at a temperature within the range 15°–120°.

6. A process as claimed in any of claim 1 wherein the reaction of the compound of formula (II) with propionic anhydride is carried out at a temperature within the range 15°–80°.

7. A process as claimed in any of claim 1 wherein subsequent reaction with methanol is carried out at a temperature within the range 50°–80°.

8. A process as claimed in any of claim 1 wherein the compound of formula (I) is isolated in the form of an acid addition salt thereof.

9. A process as claimed in claim 1 which further comprises a sodium hydroxide addition step, wherein the sodium hydroxide acts as a phase separator.

10. A process as claimed in claim 8 wherein the compound of formula (I) is isolated in the form of an oxalate salt.

* * * * *